(12) United States Patent
Van Rensburg

(10) Patent No.: US 6,913,018 B2
(45) Date of Patent: Jul. 5, 2005

(54) CONDOM DONNING DEVICE

(75) Inventor: Willem Nicolaas Van Rensburg, Cape Town (ZA)

(73) Assignee: Wincotrade Twenty (Proprietary) Limited, Bellville (ZA)

( * ) Notice: Subject to any disclaimer, the term of this patent is extended or adjusted under 35 U.S.C. 154(b) by 0 days.

(21) Appl. No.: 10/468,389

(22) PCT Filed: Mar. 7, 2002

(86) PCT No.: PCT/IB02/00673

§ 371 (c)(1),
(2), (4) Date: Feb. 2, 2004

(87) PCT Pub. No.: WO02/069861

PCT Pub. Date: Sep. 12, 2002

(65) Prior Publication Data

US 2004/0103901 A1 Jun. 3, 2004

(30) Foreign Application Priority Data

| Mar. 7, 2001 | (ZA) | 2001/1888 |
| Jun. 22, 2001 | (ZA) | 2001/5149 |
| Sep. 7, 2001 | (ZA) | 2001/7394 |
| Oct. 18, 2001 | (ZA) | 2001/8548 |

(51) Int. Cl.[7] .................................................. A61F 6/01
(52) U.S. Cl. ...................... 128/844; 128/842; 128/918; 604/327; 604/346; 604/347; 604/349; 206/69
(58) Field of Search ................................ 128/842, 844, 128/918; 206/69; 604/327, 346, 347, 349

(56) References Cited

U.S. PATENT DOCUMENTS

| 4,875,491 A | | 10/1989 | Parrone | |
| 4,972,850 A | * | 11/1990 | Broad, Jr. | 128/844 |
| 5,170,887 A | | 12/1992 | Potts et al. | |
| 5,351,698 A | * | 10/1994 | Wheeler et al. | 128/844 |
| 5,437,286 A | * | 8/1995 | Stratton | 128/844 |
| 5,549,120 A | | 8/1996 | Persson et al. | |
| 5,606,982 A | * | 3/1997 | Piotti | 128/842 |
| 5,638,949 A | * | 6/1997 | Jones | 206/69 |
| 5,651,374 A | | 7/1997 | Wester | |

FOREIGN PATENT DOCUMENTS

WO    WO 9932058 A1    7/1999

OTHER PUBLICATIONS

None

* cited by examiner

Primary Examiner—Henry Bennett
Assistant Examiner—Camtu Nguyen
(74) Attorney, Agent, or Firm—James H. Marsh, Jr.; Stinson Morrison Hecker, LLP

(57) ABSTRACT

A condom donning device (10) adapted for donning a condom (12) having a tubular wall that is rolled up into a hem ring (14) which is defined on the outside of the tubular wall in an initial configuration of the condom. The device (10) comprises two support formations (16) and (18) which together define an internal space through which a penis can extend and a separation axis A along which the support formations are separable. Each support formation defines a pair of hook-like holding formations (22) in which the hem ring of the condom can be received and held in an arrangement permitting unrolling of the hem ring when donning the condom. The invention extends to an assembly including the device (10), the condom (12) and a package in the form of a pouch of packaging film which is hermetically sealed to the support formations so as to form a hermetically sealed enclosure surrounding the condom.

16 Claims, 5 Drawing Sheets

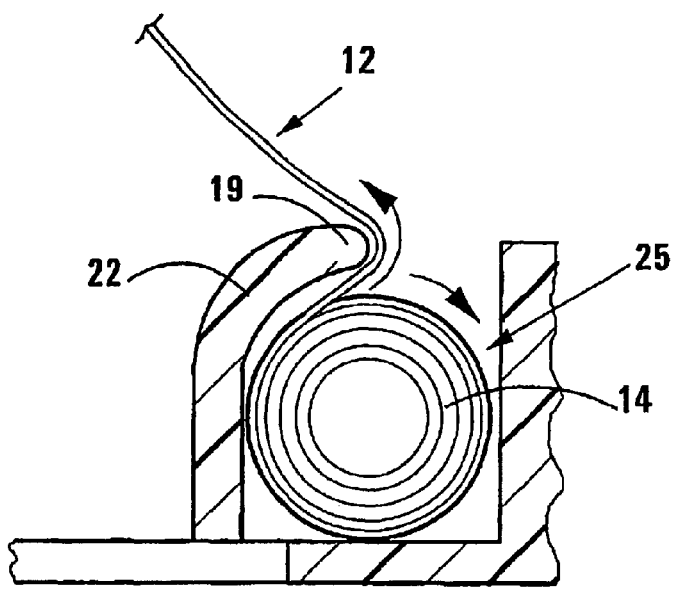
FIG 10
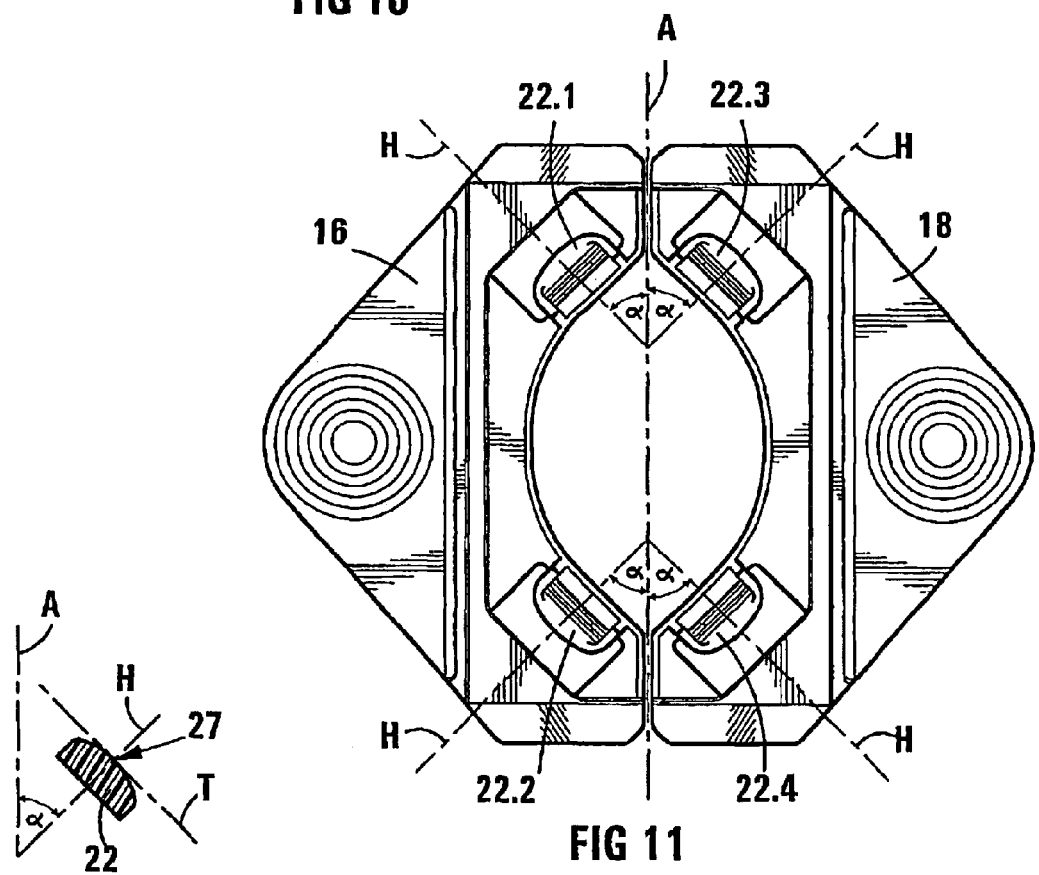
FIG 12
FIG 11

CONDOM DONNING DEVICE

FIELD OF INVENTION

THIS INVENTION relates to a condom donning device. It also relates to a condom donning device and package assembly.

BACKGROUND OF THE INVENTION

There are a number of problems associated with the packaging and use of condoms. The procedure for donning a condom manually is both cumbersome and time consuming which detracts from condoms being more widely used. Condoms are typically packed in sealed pouches and to don a condom, a user needs to tear open the pouch, ensure that the condom faces the correct way up and then roll it manually onto the penis. In tearing the pouch open a user may accidentally pinch and rupture the condom. Further, when unrolling the condom manually, difficulties have been experienced by users in applying the condom smoothly onto the penis. As a result, wrinkles often form in the condom wall which, during intercourse, may cause rupturing of the condom when the wrinkles rub against the vaginal wall.

In order to ameliorate many of the problems identified above, a number of condom application devices have been developed for donning condoms. U.S. Pat. No. 5,549,120 teaches a device for applying a condom on a penis, the device having an annular frame that is of greater width than the penis and having a seating formation in which a "rolled up" portion of the condom or hem ring which is formed on an internal side of the wall of the condom, is seated. The annular frame has a slit which allows separation of two halves of the frame for facilitating removal of the frame. U.S. Pat. No. 5,606,982 discloses an applicator device for applying a condom having a hem ring defined on an internal side of the wall of the condom. The device has an annular body on which the condom is held in an arrangement permitting unrolling of the condom for donning the condom. U.S. Pat. No. 5,170,887 discloses a condom package and donning device which comprises an enclosure and condom attachment means. When the enclosure is removed, the condom opening is exposed for donning. The device includes an annular ridge or hook attachment means for holding the hem ring of the condom which is bunched up inside the enclosure. The condom is not rolled up into a hem ring and as such, the annular ridge or hook attachments merely hold the flange or ring defined at the base of the condom, while the condom is being donned.

It is an object of the present invention to ameliorate the above identified problems.

SUMMARY OF INVENTION

According to a first aspect of the invention there is provided a condom donning device for donning a condom on an erect penis, the condom having a tubular wall having an inner side and an outer side and which is rolled up into an elastic hem ring which defines an entrance opening and which is formed on the outside of the tubular wall in an initial configuration of the condom, the condom donning device comprising:

first and second condom support formations which together define an internal space through which an erect penis can extend, the support formation defining a separation axis and being separable in a direction substantially perpendicular to the separation axis, each support formation defining at least one hook-like holding formation in which the hem ring of the condom can be received in an arrangement wherein the hook-like holding formation extend into the entrance opening of the condom and are disposed adjacent an inner side of the tubular wall thereof, each hook-like holding formation having a curved profile in which the hem ring of the condom can be received and held in an arrangement permitting unrolling of the hem ring of the condom when the support formations are displaced along the shaft of the penis for unrolling and donning the condom, in use, each hook-like holding formation defining a convexly curved condom contacting surface which contacts the inner side of the tubular wall of the condom and which conforms to the rounded shape of the hem ring of the condom, each support formation defining at least one restraining formation which is positioned on the support formation to prevent displacement of the hem ring of the condom in a direction away from the hook-like formations, thereby to resist removal of the hem ring of the condom from the holding formation during unrolling of the condom, in use.

Each support formation may define a pair of discrete, spaced hook-like holding formations.

Each hook-like holding formation may define a hook axis extending along a centre line through the holding formation when viewed in plan view, the hook axis extending through an apex of said convexly-curved condom contacting surface and perpendicularly with respect to a tangent meeting said apex, the hook axis forming an angle of 45 degrees with respect to the separation axis when viewed in plan view.

Each condom support formation may define a body portion defining said hook-like formations and a flap-like handle portion which extends from the body portion and which can be held by user for manipulating the body portion when donning a condom.

Each condom support formation may have a hinge between the body portion and the handle portion, thereby permitting hinged displacement of the handle portion relative to the body portion.

The condom donning device may be of a deformable material and the hinge of each condom support formation may be in the form of a narrowing defined between the body portion and the handle portion, which is sufficient to permit bending of the handle portion relative to the body portion.

The condom donning device may be adapted for use with a condom having a teat at an end of the condom remote from the hem ring, the condom donning device including a strip having two ends, which is connected at its ends to the condom support formations and which extends between the condom support formations and over a condom held thereon, in use, in an arrangement wherein the teat is kept folded over by the strip so as to prevent the teat from filling with air, the strip having a region of weakness which permits it to be ruptured when the support formations are separated, in use.

According to a second aspect of the invention there is provided a condom donning device and package assembly comprising a condom having a tubular wall having an inner side and an outer side and which is rolled up into an elastic hem ring which defines an entrance opening and which is formed on the outside of the tubular wall in an initial configuration of the condom;

a condom donning device for donning the condom on an erect penis, the condom donning device comprising first and second condom support formations which together define an internal space through which an erect penis can extend, the support formations defining a separation axis and being separable in a direction substantially perpendicular to the separation axis, each support formation defining at least one hook-like holding formation in which the hem ring of the condom is received and held in an arrangement wherein the hook-like holding formations extend into the entrance opening of the condom and are disposed adjacent an inner side of the tubular wall thereof, each hook-like holding formation having a curved profile in which the hem ring of the condom is received and held in an arrangement permitting unrolling of the hem ring of the condom when the support formations are displaced along the shaft of the penis for unrolling and donning the condom, in use each holding formation defining a convexly—curved condom contacting surface which contacts the inner side of the tubular wall of the condom and which conforms to the rounded shape of the hem ring, each support formation defining at least one restraining formation which is positioned on the support formation to prevent displacement of the hem ring of the condom in a direction away from the hook-like formations, thereby to resist removal of the hem ring of the condom from the holding formations during initial stages of unrolling of the condom, in use; and a package in the form of a pouch of packaging film in which the condom and at least the hook-like holding formations and the restraining formations of the support formations are contained, the package including two pouch halves which define a line of weakness between them which is in register with the separation axis along which the support formations are separable, in use, the line of weakness permitting rupturing of the package along said line of weakness when the support formations are separated from one another, in use.

Each support formation of the condom donning device may define a pair of discrete, spaced hook-like holding formations wherein each holding formation of one support formation is disposed substantially opposite a holding formation of the other support formation along a hook axis extending at an angle of 45 degrees relative to the separation axis.

Each condom support formation of the condom donning device may define a body portion defining said hook-like formations and a flap-like handle portion which extends from the body portion and which can be held by a user for manipulating the body portions when donning a condom.

Each condom support formation may have a hinge between the body portion and the handle portion, thereby permitting hinged displacement of the handle portion relative to the body portion.

The condom donning device may be of a deformable material and the hinge of each condom support formation may be in the form of a narrowing disposed between the body portion and the handle portion, which is sufficient to permit bending of the handle portion relative to the body portion.

The condom donning device may be adapted for use with a condom having a teat at an end of the condom remote from the hem ring, the condom donning device including a strip having two ends, which is connected at its ends to the condom support formations and which extends between the condom support formations and over a condom held thereon, in use, in an arrangement wherein the teat is kept folded over by the strip so as to prevent the teat from filling with air, the strip having a region of weakness which permits it to be ruptured when the support formations are separated, in use.

The packaging film may be hermetically sealed to the body portions of the support formations thereby forming a hermetically sealed enclosure surrounding the hook-like holding formations, the condom and the restraining formations, with the handle portions of the support formations extending externally of the packaging film where the handle formations can be manipulated, in use.

The packaging film may tautly span the body portions of the support formations with operative inner ends of the body portions contacting one another along said separation axis in an arrangement wherein said inner ends can be displaced operatively upwardly or downwardly via manipulation of the handle portions, to so as to exert a force on an inner side of the packaging film sufficient to rupture said line of weakness of the packaging film.

BRIEF DESCRIPTION OF THE DRAWINGS

Further features of the invention are described hereinafter by way of a non-limiting example of the invention, with reference to and as illustrated in the accompanying diagrammatic drawings. In the drawings:

FIG. 10 shows an enlarged fragmentary schematic sectional side view of part of a support formation including the hook and restraining wall detail, illustrating the manner in which the hem ring of a condom is unrolled, in use;

FIG. 11 shows a schematic top plan view of the condom donning device of FIG. 1, illustrating the angular relationship between the hook-like formations and the separation axis A defined between the support formations; and FIG. 12 shows a fragmentary, sectional schematic top plan view of a hook-like formation of the condom donning device of FIG. 1, illustrating the angular relationship between each of the hook-like holding formations and the separation axis A.

DESCRIPTION OF PREFERRED EMBODIMENT

Figure 1:
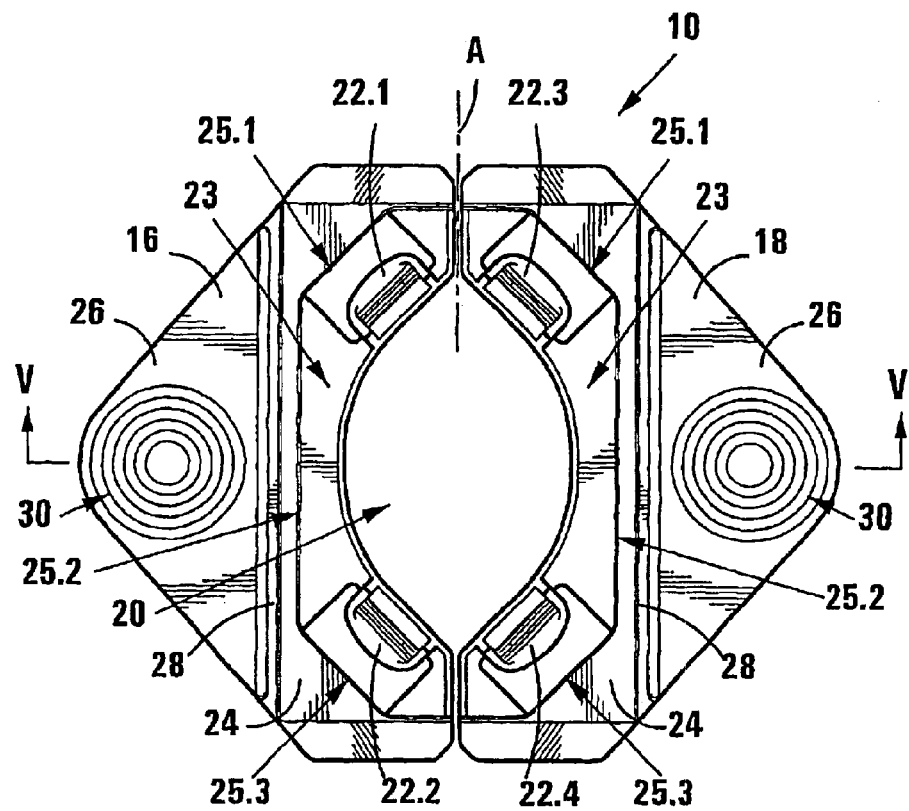
FIG. 1 shows a schematic top plan view of a condom donning device in accordance with the invention.
Figure 2:
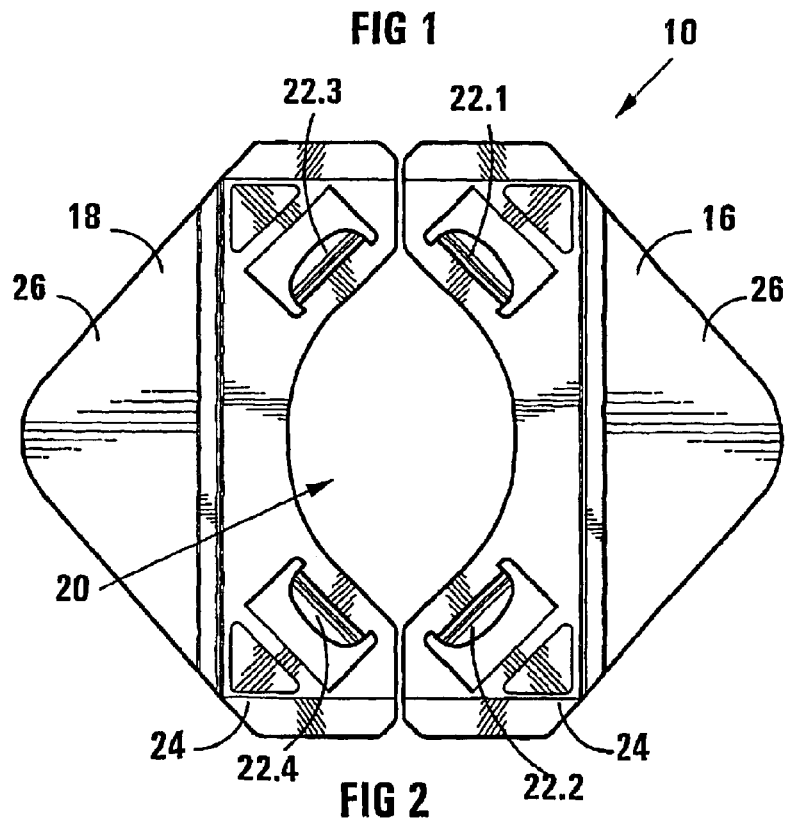
FIG. 2 shows a schematic bottom plan view of the condom donning device of FIG. 1.
Figure 3:
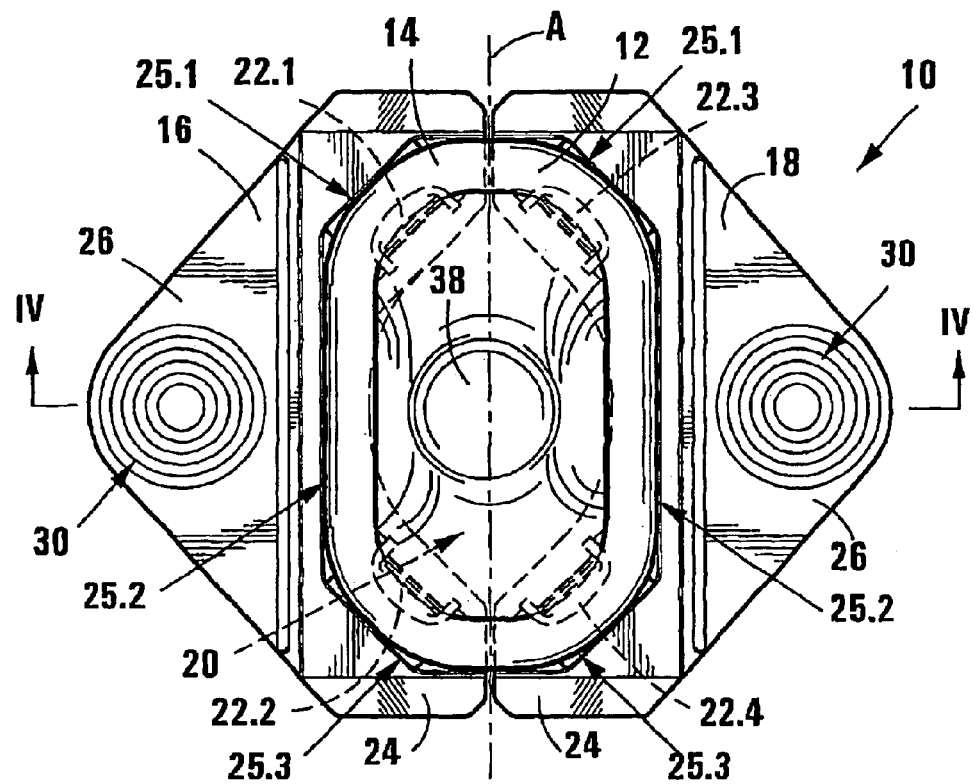
FIG. 3 shows a schematic top plan view of the condom donning device of FIG. 1, illustrating the manner in which a condom is supported thereon in an initial configuration of the condom.
Figure 4:
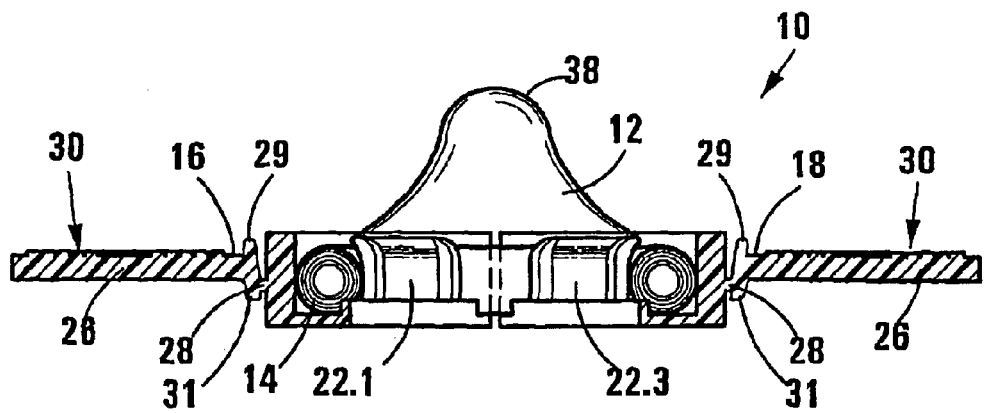
FIG. 4 shows a schematic sectional side view of the condom donning device of FIG. 1, sectioned along section line IV—IV of FIG. 3, illustrating the manner in which a condom supported thereon is unrolled, in use.
Figure 5:
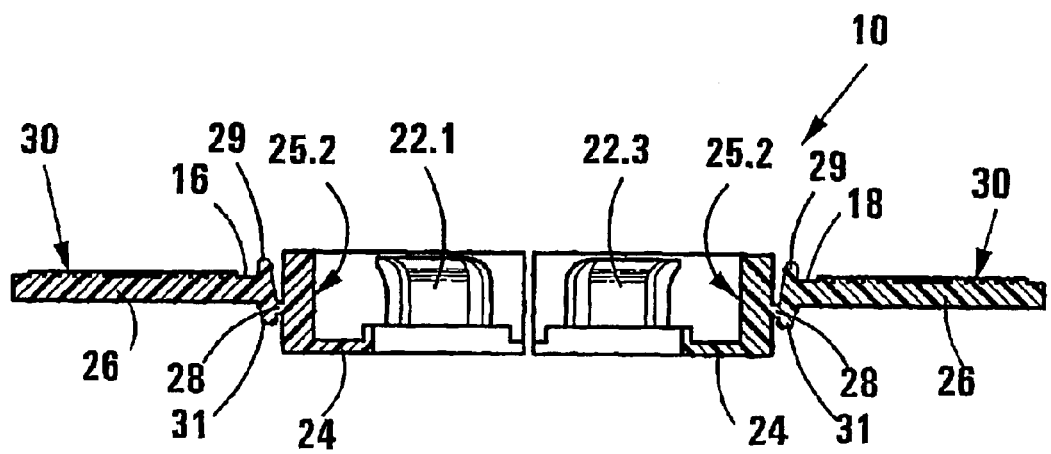
FIG. 5 shows a schematic sectional side view of the condom donning device of FIG. 1, sectioned along section line V—V of FIG. 1.

With reference to the drawings, a condom donning device in accordance with the invention, is designated generally by the reference numeral 10. The condom donning device is of a deformable plastics material and is adapted for use in donning a condom 12 on an erect penis; The condom has a latex tubular wall having an inner side and an outer side and is rolled up into an elastic hem ring 14 which defines an entrance opening and which is formed on the outside of the tubular wall in an initial configuration of the condom. The outer side of the tubular wall of the condom is lubricated and the inner side of the tubular wall is lubricated up to a region terminating short of the free end of the condom remote from the hem ring 14. The lack of lubrication on the inner side of the wall at the free end of the condom allows the condom to grip the glans of a penis on which a condom is donned, in use.

The condom donning device 10 has two halves in the form of a first condom support formation 16 and a second condom support formation 18. Similar and the same features of the condom support formations 16 and 18 are designated by similar and the same reference numerals, respectively, in the drawings. The support formations together define an internal space 20 through which a penis can extend when donning the condom, in use. The support formations together define a separation axis A. The support formations are separable in a direction substantially perpendicular to the separation axis in order to enlarge the internal space 20 for accommodating a penis therein, in use.

The condom support formation 16 defines a pair of discrete, spaced hook-like holding formations 22.1 and 22.2 and the condom support formation 18 similarly defines a pair of discrete, spaced hook-like formations 22.3 and 22.4 in which the hem ring 14 of the condom 12 can be received in an arrangement wherein the hook-like holding formations extend into the entrance opening of the condom and are disposed adjacent an inner side of the tubular wall thereof. Each hook-like holding formation 22 has a curved hook-like profile when viewed from a side thereof, in which the hem ring of the condom 12 can be received and held in an arrangement permitting unrolling of the hem ring of the condom when the support formations are displaced along the shaft of a penis for unrolling and donning the condom, in use.

Each hook-like holding formation 22 defines a convexly curved condom-contacting surface which contacts the inner side of the tubular wall of the condom and which conforms to the rounded shape of the hem ring 14 of the condom 12.

Each of the condom support formations 16 and 18 defines a recess 23 in which the hook-like formations are disposed. The recess 23 is surrounded by a restraining wall comprising restraining wall sections 25.1, 25.2 and 25.3 The restraining wall sections 25.1 and 25.3 are disposed opposite the hook-like formations, while the restraining wall formation 25.2 extends between the wall sections 25.1 and 25.3 The restraining wall sections together restrain the hem ring 14 of the condom 12 from moving outwardly away from the hook-like formations and thus ensure that the hem ring remains captured by the hook-like formations.

With reference to FIG. 11 of the drawings, the hook-like formations 22 each define a hook axis H which extends along a centre line through the hook-like formation when viewed in plan view and intersecting the separation axis A at an angle "α" of 45 degrees. More particularly and referring also to FIG. 12 of the drawings, the hook axis H of each hook-like formation extends along said centre line through a apex 27 of said convexly-curved condom contacting surface of the hook-like formation and extends perpendicularly with respect to a tangent T meeting the apex of the convexly-curved condom contacting surface of the hook-like formation.

Each of the condom support formations 16 and 18 defines a body portion 24 which defines the recess 23 and the hook-like formations 22, and a flap-like handle portion 26 which extends from the body portion and which can be held by a user for manipulating the body portion when donning a condom, in use. Each condom support formation defines a hinge between the body portion 24 and the handle portion 26 which permits hinged displacement of the handle portion 26 relative to the body portion 24. The hinge of each condom support formation is in the form of a narrowing 28 defined between the relevant body portion and the handle portion, which is sufficiently narrow to permit bending of the handle portion relative to the body portion. Each handle portion 26 defines a gripping formation in the form of a set of ridges 30 defined by concentric circles disposed on an upper surface of the handle portion. Each handle formation 26 defines elongate ridge formations 29 and 31 at operative upper and lower sides, respectively, of the handle portion adjacent said narrowing 28. The longitudinal ridges 29 and 31 act as stops limiting further hinged displacement of the handle portions relative to the body portions when the ridges 29 and 31 contact side walls of the body portions, in use.

The condom donning device includes a strip 32 having two ends 34.1 and 34.2, which is connected at its ends to the body portions 24 of the condom support formations 16 and 18 and which extends between the condom support formation 16 and 18 and over the condom 12 held thereon. The condom 12 has a teat 38 defining a receptacle for semen, at an end thereof remote from the hem ring 14. The strip 32 is of a stretchable plastics material and defines a line of weakness 36 which is in register with the separation axis A of the condom support formation and which permits rupturing of the strip when the support formations are separated, in use. More particularly, the strip is of a material and has a thickness which permits a degree of stretching before rupturing, thereby allowing initial separation of the support formations so as to allow the insertion of glans of a penis into the condom while the teat 38 is held in a folded-over configuration by the strip 32. Further separation of the support formations causes rupturing of the strip 32. The strip 32 extends between the condom support formations in an arrangement wherein the teat of the condom is held in a folded-over configuration by the strip 32 so as to prevent the teat from filling with air prior to insertion of a penis into the condom, in use.

Figure 6:
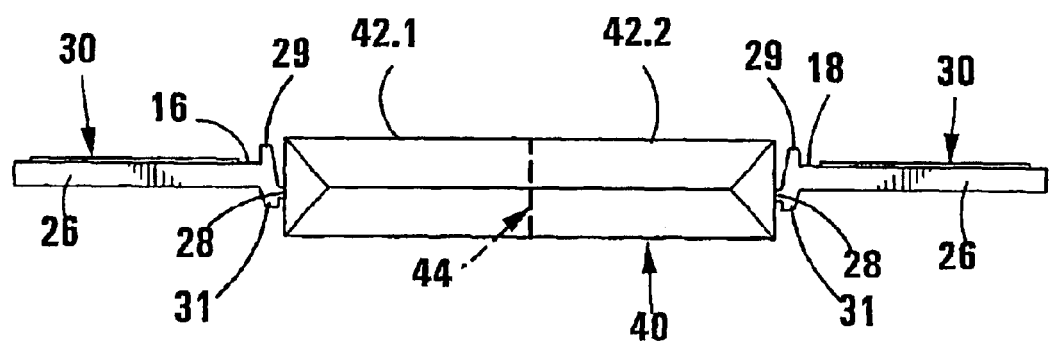
FIG. 6 shows a schematic side view of a condom donning device and package assembly in accordance with the invention.
Figure 7:
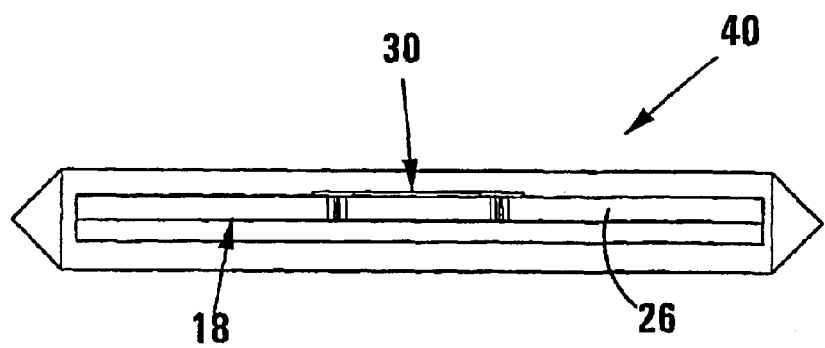
FIG. 7 shows a schematic end view of the condom donning device and package assembly of FIG. 6.
Figure 8:
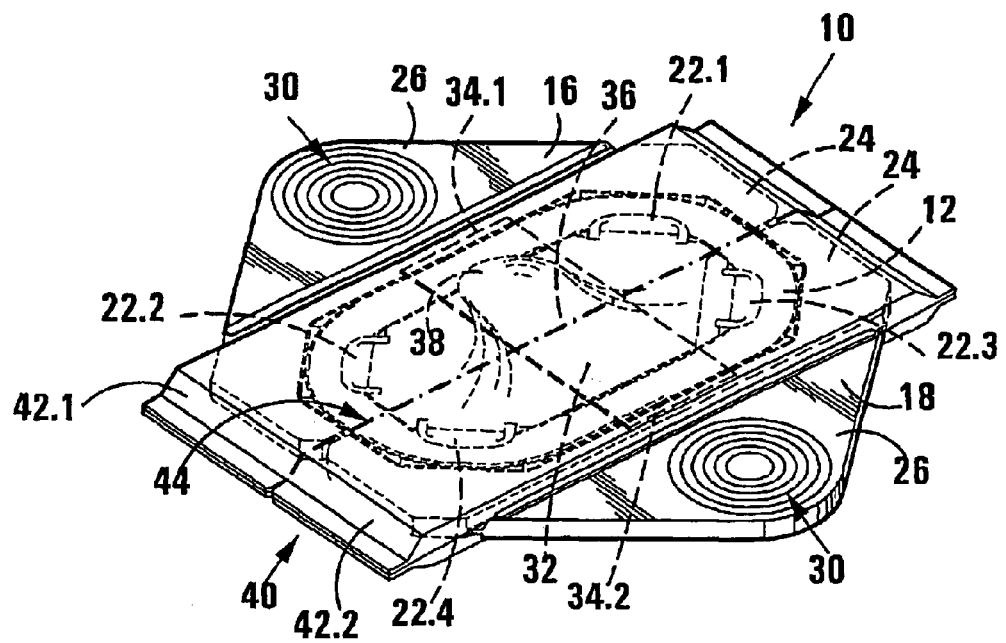
FIG. 8 shows a schematic perspective view of the condom donning device and package assembly of FIG. 6.
Figure 9:
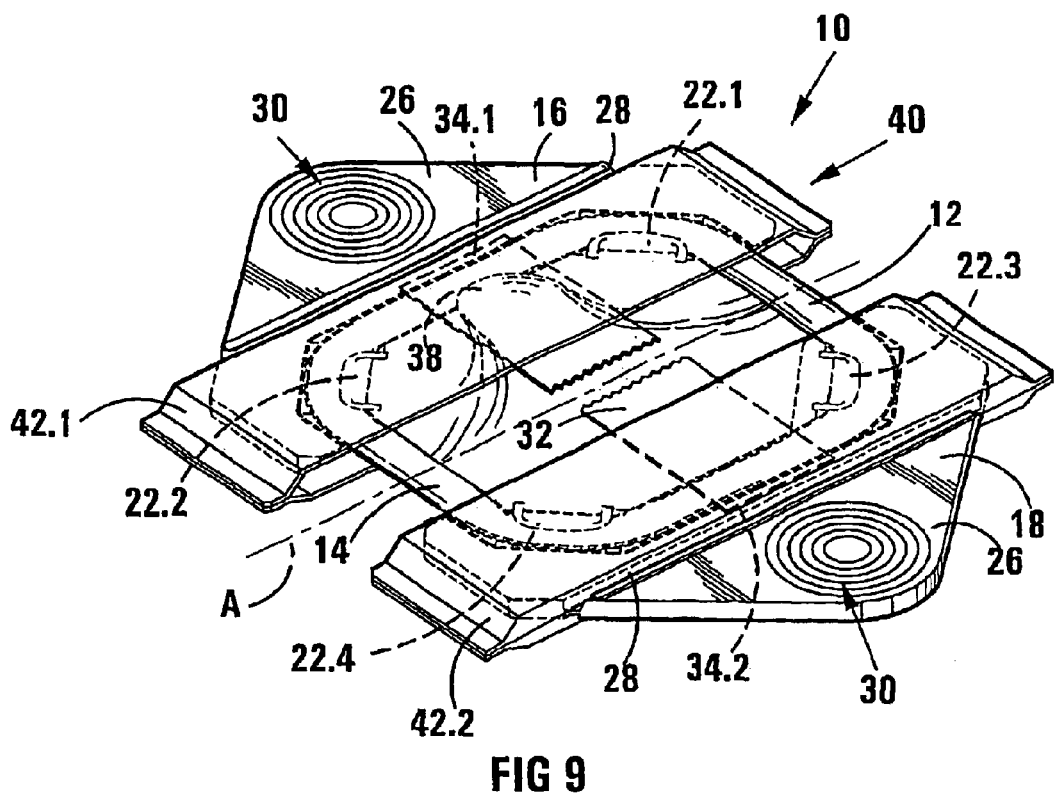
FIG. 9 shows a schematic perspective view of the condom donning device and package assembly of FIG. 6, in an open configuration wherein the support formations are separated along separation axis A.

The invention extends to a condom donning device and package assembly as is illustrated in FIGS. 6, 7, 8 and 9 of the drawings. The condom donning device and package assembly comprises the condom 12, the condom donning device 10 and a package which is in the form of a pouch of packaging film designated generally by the reference numeral 40. The pouch includes two pouch halves 42.1 and 42.2 which define a line of weakness 44 between them which is in register with the separation axis A along which the support formations are separable, in use. The line of weakness 44 permits rupturing of the package along the line of weakness when the support formations are separated from one another, in use. More particularly, the packaging film of the pouch tautly spans the body portions 24 of the condom support formation. Operative inner ends of the body portions contact one another along the separation axis A in an arrangement wherein the body portions can be levered with respect to one another via the inner ends thereof for displacing the inner ends of the body portions upwardly or downwardly relative to one another, via manipulation of the handle portions, so as to exert a force on an inner side of the packaging film for rupturing the line of weakness 44.

In use, when donning the condom 12 on a penis, the inner ends of the body portion of the support formations 16 and 18 are levered with respect to one another, via manipulation of the handle portions 26, thereby displacing the inner ends operatively upwardly or downwardly. This exerts a force on an inner side of the packaging 40 causing rupturing of the line of weakness 44. This allows separation of the support formations 16 and 18 perpendicular to the separation axis A, when viewed in plan view. The strip 32, being of a stretchable material allows a degree of stretching before rupturing along its line of weakness 36, thereby allowing initial separation of the support formation so as to permit insertion of the glans of the penis into the condom while the teat 38 continues to be held in a folded-over configuration by the strip 32. Further separation of the support formations causes rupturing of the strip 32. Thereafter, the support formations 16 and 18 are slid down the length of the penis, with the hem ring being received and held by the hook-like holding formations 22 in an arrangement which permits unrolling of the hem ring 14 of the condom. Lubricants applied to inner and outer sides of the wall of the condom allow the layers of the wall of the condom to slide over one another and assist in reducing friction caused by contact between the wall of the condom and each of the hook-like holding formations 22.

With the hem ring 14 being formed on the outside of the tubular wall of the condom, the region of the wall of the condom which is being unrolled from the hem ring contacts the convexly-curved condom contacting surface of the condom. It will be appreciated that when the hem ring is being unrolled when the donning the condom, the free end regions 19 of the hook-like holding formations will exert a force on the hem ring 14 in a direction towards the base of the penis. The Applicant has found that the shape of the hook-like holding formation and the fact that the hem ring 14 is defined on the outside of the tubular wall of the condom minimise, friction between the hem ring and the hook-like holding formation when the hem ring is unrolled. In this arrangement, the portion of the condom wall which is being unrolled makes contact with the condom contacting surface of the hook-like holding formation. In contrast thereto, the Applicant has found that with condoms having the hem ring defined on an inner side of the tubular wall, there is, because of the curved shape of the tightly wound hem ring, a relatively smaller area of contact between the hem ring and the hook-like holding formation than in the case of the present invention where the unravelling region of the hem ring 14 contacts the hook-like holding formation over a greater surface area. The reduced contact surface area results in increased pressure which in turn increases the co-efficient friction of friction between the hem ring and the hook-like holding formation. Furthermore, the Applicant has found that the angular relationship between the hook-like holding formations and the separation axis A of the support formation is an optimal one in terms of further reducing the co-efficient friction of friction between the unravelling hem ring 14 and the hook-like formations. In particular, at the optimum angle of 45 degrees defined between the hook axis H and the separation axis A, the contact surface area between the hem ring and the hook-like holding formation will be greatest, thereby preventing high pressure contact areas from forming.

What is claimed is:

1. A condom donning device for donning a condom on an erect penis, the condom having a tubular wall having an inner side and an outer side and which is rolled up into an elastic hem ring which defines an entrance opening and which is formed on the outside of the tubular wall in an initial configuration of the condom, the condom donning device comprising:

first and second condom support formations for defining an internal space through which an erect penis can extend, the support formations defining a separation axis and being separable in a direction substantially perpendicular to the separation axis, each support formation defining at least one hook-like holding formation in which the hem ring of the condom can be received in an arrangement wherein the hook-like holding formation extend into the entrance opening of the condom and are disposed adjacent an inner side of the tubular wall thereof, each hook-like holding formation having a curved profile in which the hem ring of the condom can be received and held in an arrangement permitting unrolling of the hem ring of the condom when the support formations are displaced along the shaft of the penis for unrolling and donning the condom, in use, each hook-like holding formation defining a condom contacting surface which contacts the inner side of the tubular wall of the condom and which conforms to the shape of the hem ring, the condom contacting surface contacting the hem ring in an area where the hem ring extends through an arc, each support formation defining at least one restraining formation which is positioned on the support formation to prevent displacement of the hem ring of the condom in a direction away from the hook-like formations, thereby to resist removal of the hem ring of the condom from the holding formation during unrolling of the condom, in use.

2. A condom donning device as claimed in claim 1, wherein each support formation defines a pair of discrete, spaced hook-like holding formations.

3. A condom donning device as claimed in claim 2, wherein each hook-like holding formation defines a hook axis extending along a centre line through the holding formation when viewed in plan view, the hook axis extending perpendicularly with respect to a tangent to the condom contacting surface, and the hook axis forming an angle of 45 degrees with respect to the separation axis when viewed in plan view.

4. A condom donning device as claimed in claim 1, wherein each condom support formation defines a body portion defining said hook-like formations and a flap-like handle portion which extends from the body portion and which can be held by user for manipulating the body portion when donning a condom.

5. A condom donning device as claimed in claim 4, wherein each condom support formation has a hinge between the body portion and the handle portion, thereby permitting hinged displacement of the handle portion relative to the body portion.

6. A condom donning device as claimed in claim 5, which is of a deformable material and wherein the hinge of each condom support formation is in the form of a narrowing defined between the body portion and the handle portion, which is sufficient to permit bending of the handle portion relative to the body portion.

7. A condom donning device as claimed in claim 1, which is adapted for use with a condom having a teat at an end of the condom remote from the hem ring, the condom donning device including a strip having two ends, which is connected at its ends to the condom support formations and which extends between the condom support formations and over a condom held thereon, in use, in an arrangement wherein the teat is kept folded over by the strip so as to prevent the teat from filling with air, the strip having a region of weakness which permits it to be ruptured when the support formations are separated, in use.

8. A condom donning device and package assembly comprising:

a condom having a tubular wall having an inner side and an outer side and which is rolled up into an elastic hem ring which defines an entrance opening and which is formed on the outside of the tubular wall in an initial configuration of the condom;

a condom donning device for donning the condom on an erect penis, the condom donning device comprising first and second condom support formations for defining an internal space through which an erect penis can extend, the support formations defining a separation axis and being separable in a direction substantially perpendicular to the separation axis, each support formation defining at least one hook-like holding formation in which the hem ring of the condom is received and held in an arrangement wherein the hook-like holding formations extend into the entrance opening of the condom and are disposed adjacent an inner side of the tubular wall thereof, each hook-like holding formation having a curved profile in which the hem ring of the condom is received and held in an arrangement permitting unrolling of the hem ring of the condom when the support formations are displaced along the shaft of the penis for unrolling and donning the condom, in use, each holding formation defining a condom contacting surface which contacts the inner side of the tubular wall of the condom and which conforms to the shape of the hem ring, the condom contacting surface contacting the hem ring in an area where the hem ring extends through an arc, each support formation defining at least one restraining formation which is positioned on the support formation to prevent displacement of the hem ring of the condom in a direction away from the hook-like formations, thereby to resist removal of the hem ring of the condom from the holding formations during initial stages of unrolling of the condom, in use; and a package in the form of a pouch of packaging film in which the condom and at least the hook-like holding formations and the restraining formations of the support formations are contained, the package including two pouch halves which define a line of weakness between them which is in register with the separation axis along which the support formations are separable, in use, the line of weakness permitting rupturing of the package along said line of weakness when the support formations are separated from one another, in use.

9. A condom donning device and package assembly as claimed in claim 8, wherein each support formation of the condom donning device defines a pair of discrete, spaced hook-like holding formations.

10. A condom donning device and package assembly as claimed in claim 9, wherein each hook-like holding formation defines a hook axis extending along a centre line through the holding formation when viewed in plan view, the hook axis extending perpendicularly with respect to a tangent to the condom contacting surface, and the hook axis forming an angle of 45 degrees with respect to the separation axis when viewed in plan view.

11. A condom donning device and package assembly as claimed in claim 8, which is adapted for use with a condom having a teat at an end of the condom remote from the hem ring, the condom donning device including a strip having two ends, which is connected at its ends to the condom support formations and which extends between the condom support formations and over a condom held thereon, in use, in an arrangement wherein the teat is kept folded over by the strip so as to prevent the teat from filling with air, the strip having a region of weakness which permits it to be ruptured when the support formations are separated, in use.

12. A condom donning device and package assembly as claimed in claim 8, wherein each condom support formation of the condom donning device defines a body portion defining said hook-like formations and a flap-like handle portion which extends from the body portion and which can be held by a user for manipulating the body portions when donning a condom.

13. A condom donning device and package assembly as claimed in claim 12, wherein each condom support formation has a hinge between the body portion and the handle portion, thereby permitting hinged displacement of the handle portion relative to the body portion.

14. A condom donning device and package assembly as claimed in claim 13, which is of a deformable material and wherein the hinge of each condom support formation is in the form of a narrowing disposed between the body portion and the handle portion, which is sufficient to permit bending of the handle portion relative to the body portion.

15. A condom donning device and package assembly as claimed in claim 12, wherein the packaging film is hermetically sealed to the body portions of the support formations thereby forming a hermetically sealed enclosure surrounding the hook-like holding formations, the condom and the restraining formations, with the handle portions of the support formations extending externally of the packaging film where the handle formations can be manipulated, in use.

16. A condom donning device and package assembly as claimed in claim 12, wherein the packaging film tautly spans the body portions of the support formations, with operative inner ends of the body portions contacting one another along said separation axis in an arrangement wherein the body portions can be levered with respect to one another via the inner ends thereby displacing the inner ends operatively upwardly or downwardly, via manipulation of the handle portions, to so as to exert a force on an inner side of the packaging film sufficient to rupture said line of weakness of the packaging film.

* * * * *